US008623311B2

(12) United States Patent
Bujoli et al.

(10) Patent No.: US 8,623,311 B2
(45) Date of Patent: Jan. 7, 2014

(54) GALLIUM-DOPED PHOSPHOCALCIC COMPOUNDS

(75) Inventors: Bruno Bujoli, Suce sur Erdre (FR); Jean-Michel Bouler, Carquefou (FR); Pascal Janvier, Nantes (FR); Ibrahim Khairoun, Nantes (FR); Verena Schnitzler, Nantes (FR)

(73) Assignees: Graftys (FR); Universite de Nantes (FR); Centre National de la Recherche Scientifique (C.N.R.S.) (FR)

(*) Notice: Subject to any disclaimer, the term of this patent is extended or adjusted under 35 U.S.C. 154(b) by 594 days.

(21) Appl. No.: 12/716,862

(22) Filed: Mar. 3, 2010

(65) Prior Publication Data

US 2010/0269734 A1    Oct. 28, 2010

Related U.S. Application Data

(60) Provisional application No. 61/157,043, filed on Mar. 3, 2009.

(51) Int. Cl.
    *C01B 25/32* (2006.01)
(52) U.S. Cl.
    USPC .......................................... 423/306; 106/690
(58) Field of Classification Search
    USPC .......................................... 423/306; 106/690
    See application file for complete search history.

(56) References Cited

U.S. PATENT DOCUMENTS

| 4,529,593 | A | 7/1985 | Warrell, Jr. et al. |
| 4,880,610 | A | 11/1989 | Constantz |
| 5,053,212 | A | 10/1991 | Constantz et al. |
| 5,690,908 | A | 11/1997 | Deutsch et al. |
| 2010/0248191 | A1 | 9/2010 | Bujoli et al. |
| 2010/0269734 | A1 | 10/2010 | Bujoli et al. |

FOREIGN PATENT DOCUMENTS

| EP | 0416761 | 3/1991 |
| EP | 0543765 | 5/1993 |
| EP | 0664133 | 7/1995 |
| FR | 2715853 | 8/1995 |
| WO | WO 96/36562 | 11/1996 |
| WO | 01/49327 | 7/2001 |
| WO | WO 2004/000374 | 12/2003 |
| WO | WO 2008/023254 | 2/2008 |

OTHER PUBLICATIONS

Okamoto et al, "Studies on calcium phoshate precipitation:Effects of nmetal ions used in dental materials", Joun. Biomatl. res., vol. 28, 1994, pp. 1403-1410.*
Blumenthal et al, "The Effect of Aluminum and Galium IOns on the Minerlization Process", Bull. Hospital for Joint Diseases Orthopaedic Institute, vol. 49, #2, 1989, pp. 192-204.*

Korbas et al, "Bone Tissue incorporates in vitro gallium with local structure similar to galium-doped brushite", J. Biol lnorg. Chem, 2004, 9, pp. 67-76.*
Tung et al, "An Intermediate State in Hydrolysis of Amorphous Calciu Phsphate", Calcif Tissue Int, 35, 1983, pp. 783-790.*
Albee, F.H., "Studies in Bone Growth" Ann. Surg. (1920) 71:32-39.
Bernstein, L.R. , "Mechanism of Therapeutic Activity for Gallium" Pharmacological Reviews (1998) 50(4):665-682.
Blumenthal, N.C. et al., "The Effect of Aluminum and Gallium Ions on the Mineralization Process" Bull. Hosp. Jt. Dis. Orthop. Inst. (1989) 49:192-204.
Bockman, R.S. et al., "Treatment of Paget's Disease of Bone With Low-Dose, Subcutaneous Gallium Nitrate" J. Bone Miner. Res. (1989) 4:S167.
Bockman, R.S. et al., "Treatment of Patients With Advanced Paget's Disease of Bone With Two Cycles of Gallium Nitrate" J. Clin. Endocrinol. Metab. (1995) 80:595-602.
Bockman, R.S. et al., "A Multicenter Trial of Low Dose Gallium Nitrate in Patients with Advanced Paget's Disease of Bone" Semin. Arthritis Rheum (1994) 23:268-269.
Brown, W.E. et al., "A new calcium phosphate setting cement" J. Dent. Res. (1983) 62:672.
Dickens, B. et al., "Crystallographic Studies of the Role of Mg as a Stabilizing Impurity in beta-Ca3(PO4)2 I. The Crystal Structure of Pure beta-Ca3(PO4)2" J. Solid State Chem. (1974) 10:232.
Donnelly, R. et al., "The Effect of Gallium on Seeded Hydroxyapatite Growth" Calcif. Tissue Int. (1989) 44:138-142.
Donnelly, R. et al., "The Effect of Gallium Nitrate on Healing of Vitamin D- and Phosphate-Deficient Rickets in the Immature Rat" Calcif. Tissue Int. (1993) 53(6):400-410.
Dudley, H.C. et al., "Deposition of Radio Gallium (Ga72) in Skeletal Tissues" J. Pharmacol. Exp. Ther. (1949) 96:224-227.
Golubev et al., "On Double Phosphates Ca9M(PO4)7 (M = Al, Fe, Cr, Ga, Sc, Sb, In)" Neorganicheskoi khimii (1990) 35(12):3037-3041.
Jarcho, M., "Biomaterial Aspects of Calcium Phosphates—Properties and Applications" Dental Clinics of North America (1986) 30(1):25-47.
Korbas et al., "Bone tissue incorporates in vitro gallium with a local structure similar to gallium-doped brushite" J. Biol. Inorg. Chem. (2004) 9:67-76.
LeGeros et al., "Apatitic Calcium Phosphates: Possible Dental Material Restorative Materials" J. Dent. Res. (1982) Spec. Issue 61:343.
Mathew, M. et al., "The Crystal Structure of a-Ca3(PO4)2*" Acta Crystallogr. (1977) B33:1325.
Nelson, B. et al., "Distribution of Gallium Human Tissues After Intravenous Administration" J. Nucl. Med. (1972) 13:92-100.
Nery, E.B. et al., "Bioceramic Implants in Surgically Produced Infrabony Defects" J. Periodontol. (1975) 46:328-347.
Pompe, W. et al., "Functionally graded materials for biomedical applications" Matl. Sci. Eng. (2003) A362:40-60.

(Continued)

*Primary Examiner* — Carol M Koslow
(74) *Attorney, Agent, or Firm* — Michael Best & Friedrich LLP

(57) ABSTRACT

The present invention relates to a gallium-doped phosphocalcic compound of formula (I):

$$Ca_{(10.5-1.5x)}Ga_x(PO_4)_7 \qquad (I)$$

Figure 1:
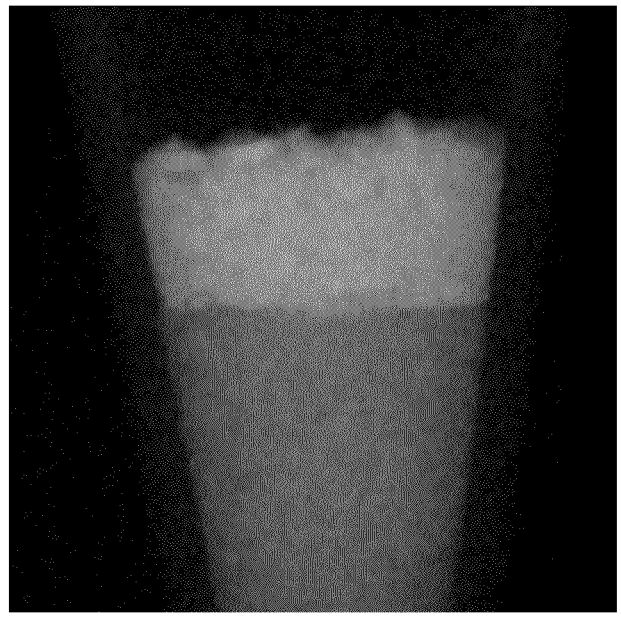

wherein 0<x<1 and the salts, hydrates and mixtures thereof.

The invention further relates to a solid state process and a process in solution for the manufacture of such compounds and the use thereof for the preparation of a biomaterial, in particular a self-setting calcium-phosphate cement (CPC).

5 Claims, 4 Drawing Sheets

(56) References Cited

OTHER PUBLICATIONS

Ray, R.D. et al., "A Preliminary Report on Studies of Basic Calcium Phosphate in Bone Replacement" Surg. Form. (1951) 429:434.

Valappil, S.P. et al., "Controlled delivery of antimicrobial gallium ions from phosphate-based glasses" Acta Biomaterialia (2008) doi:10.1016/j.actbio.2008.09.019.

Warrell, R.P. et al., "Gallium Nitrate Inhibits Calcium Resorption from Bone and Is Effective Treatment for Cancer-related Hypercalcemia" J. Clin. Invest. (1984) 73:1487-1490.

Warrell, R.P. Jr. et al., "Metabolic Effects of Gallium Nitrate Administered by Prolonged Infusion" Cancer Treat. Rep. (1985) 69:653-655.

Warrell, R.P. Jr. et al., "Gallium in the Treatment of Hypercalcemia and Bone Metastasis" in Important Advances in Oncology, DeVita, V.T. et al. eds., J.B. Lippincott, Philadelphia, PA (1989) 205-220.

Warrell, R.P. Jr. et al., "Gallium Nitrate Inhibits Accelerated Bone Turnover in Patients With Bone Metastases" J. Clin. Oncol. (1987) 5:292-298.

Warrell, R.P. Jr. et al., "Low-Dose Gallium Nitrate for Prevention of Osteolysis in Myeloma: Results of a Pilot Randomized Study" J. Clin. Oncol. (1993) 11:2443-2450.

Warrell, R.P. Jr. "Gallium for Treatment of Bone Diseases" in Handbook of Metal-Ligan Interactions in Biological Fluids, Bioinorganic Medicine, Berthon, G. editor, Marcel Dekker, New York (1995) 2:1253-1265.

Yashima, M. et al., "Crystal structure analysis of beta-tricalcium phosphate CA3(PO4)2 by neutron powder diffraction" J. Solid State Chem. (2003) 175:272.

Berthon et al, "Speciation Studies in Relation to the Bioavailability and Drug Activity of Tetracyclines", Handbook of Metal-Ligand Interactions in Biological Fluids, Bioinorganic Medicine, pp. 1252-1265, vol. 2, Part Five, Chapter 3, Section F, Marcel Dekker, New York. USA, 1995.

International Search Report and Written Opinion for PCT/EP2010/052723 dated May 3, 2010 (11 pages).

United States Patent Office Action for U.S. Appl. No. 13/255,069 dated Aug. 23, 2012 (9 pages).

United States Patent Office Restriction Requirement for U.S. Appl. No. 12/716,850 dated Sep. 12, 2012 (8 pages).

Yang et al., "The design of scaffolds for use in tissue engineering. Part I. Traditional factors," Tissue Eng. (2001) 7(6):679-689.

* cited by examiner (ppm)

GALLIUM-DOPED PHOSPHOCALCIC COMPOUNDS

CROSS-REFERENCE TO RELATED APPLICATIONS

This application claims the benefit of priority to U.S. Provisional Application No. 61/157,043 filed Mar. 3, 2009, the entire disclosure of which is herein incorporated by reference in its entirety for any purpose.

FIELD OF THE INVENTION

The invention relates to new gallium-doped phosphocalcic compounds and to processes of manufacture thereof.

BACKGROUND OF THE INVENTION

Bone is a composite of biopolymers, principally collagen, and an inorganic component identified as carbonate hydroxyapatite, approximated as $(Ca,Mg,Na,M)_{10}(PO_4, CO_3,HPO_4)_6(OH,Cl)_2$.

Deregulation of the bone activity of an individual is the cause of many bone pathologies such as osteoporosis, Paget's disease or osteolytic tumors. Taking into account, in particular, the increase in human life expectancy, osteoporosis has become a public health problem and much research has been undertaken to remedy it. Since the bone pathologies under consideration are caused by an imbalance in bone remodeling to the benefit of the activity of osteoclasts, one of the routes of treatment envisioned consisted in reducing the activity of osteoclasts, in order to slow down the degradation of the bone material.

Gallium has long been known to concentrate in skeletal tissue, particularly regions of bone deposition and remodeling (e.g., Dudley and Maddox, 1949; Nelson et al., 1972). However, very little information exists on mechanisms of gallium uptake by bone cells and the mechanisms of skeletal gallium accumulation remain largely unknown. Gallium is known to adsorb in vitro to synthetic hydroxyapatite and as a result crystallization and probably dissolution of hydroxyapatite is decreased (Donnelly and Boskey, 1989; Blumenthal and Cosma, 1989). In a recent study, Korbas et al., 2004, reported experiments in which bone tissue incorporates gallium in vitro with a local structure similar to brushite. The gallium doped model compounds disclosed have a Ca/P molar ratio of 1 (ACP and brushite) and 1.66 (AHP).

Many studies have shown that gallium inhibits bone resorption and lowers plasma calcium through its antiresorptive activity (e.g., Warrell et al., 1984, 1985; Warrell and Bockman, 1989; Bernstein, L. R. 1998). For example, U.S. Pat. No. 4,529,593 discloses a method effective against excessive loss of calcium from bone using a gallium compound, such as gallium nitrate. The excessive loss of calcium may be linked to hypocalcaemia, osteoporosis or hyperparathyroidism. The gallium compound is administered intravenously, subcutaneously or intramuscularly.

Based on its antiresorptive activity, gallium has also been used in the clinical treatment of hypocalcaemia of malignancy (Warrell and Bockman, 1989) and Paget's disease of bone (Bockman and Bosco, 1994; Bockman et al., 1989, 1995). Gallium has also shown clinical efficiency in suppressing osteolysis and bone pain associated with multiple myeloma and bone metastases (Warrell et al., 1987, 1993), and has been suggested as a treatment for osteoporosis (Warrell, 1995). In vitro efficiency as antibacterial agent has also been reported (Valappil, 2008).

Gallium nitrate is currently marketed as Ganite™, which product is administered through intravenous injection for the treatment of clearly symptomatic cancer-related hypocalcaemia that has not responded to adequate hydration. According to the FDA approved labelling for Ganite™, gallium nitrate exerts a hypocalcemic effect by inhibiting calcium resorption from bone, possibly by reducing increased bone turnover. Indeed, gallium may have an inhibitory effect on osteoclasts responsible for bone resorption and an increasing effect on osteoblasts responsible for bone growing without cytotoxic effect on bone cells (Donnelly, R., et al., 1993).

The compound of formula $Ca_9Ga(PO_4)_7$ was reported by Golubev et al., 1990 and studied through X-ray diffraction and IR spectroscopy.

TECHNICAL PROBLEM

As a result of its present systemic administration route, gallium shows a low level of absorption onto bone material along with a high potential for side effects.

There is thus a need for providing an alternative administration route for gallium, in particular for the treatment of bone diseases such as osteoporosis, Paget's disease or osteolytic tumors, which overcomes one or more of the above drawbacks. There is a particular interest to provide such a route which allows a precise tuning of the gallium release in terms of dosage and duration according to therapeutic needs.

SUMMARY OF THE INVENTION

According to the present invention are provided novel gallium-doped phosphocalcic compounds.

The present inventors have surprisingly shown that it is possible to include Ga(III) ions in a phosphocalcic compound. Further, it has been shown that such gallium modified phosphocalcic compounds are capable of releasing gallium in situ.

Finally, the use of gallium doped calcium phosphate compounds with a molar ratio Ca/P comprised between 1.28 and 1.5 allows for optimal gallium release characteristics. Indeed, highly water soluble calcium phosphate compounds such as gallium doped brushite (Ca/P=1) is expected to exhibit a rapid gallium release and thus a short activity span with a risk of overdosage while sparingly water soluble calcium phosphate compounds such as gallium doped hydroxyapatite (HAP) (Ca/P=1.66) is expected to exhibit a gallium release which may be insufficient for any therapeutic effect.

The gallium-doped phosphocalcic compounds may thus be included in biomaterials such as self setting calcium phosphate cements (CPC). Such biomaterials may be introduced directly into the body by injection where they are capable of releasing locally gallium in situ upon degradation by bone cells, close to the site in need thereof. In this respect, it was possible to obtain a slow gallium release over a long time period.

The gallium-doped phosphocalcic compounds according to the invention are thus particularly suitable for the manufacture of biomaterials useful for the treatment of bone diseases.

According to a second aspect, the invention further proposes processes for the manufacture of the novel gallium-doped phosphocalcic compounds.

The first process for the manufacture of gallium-doped phosphocalcic compounds according to the invention is a solid state process wherein a calcium phosphate is sintered in the presence of calcium carbonate and a gallium compound.

The second process for the manufacture of gallium-doped phosphocalcic compounds according to the invention is a process in solution wherein the calcium phosphate is precipitated from an aqueous solution also containing a gallium compound.

DEFINITIONS

In the context of the present invention, the term "phosphocalcic" or "calcium phosphate" refers to minerals containing calcium ions ($Ca^{2+}$) together with orthophosphate ($PO_4^{3-}$), metaphosphate or pyrophosphate ($P_2O_7^{4-}$) and occasionally other ions such as hydroxide ions or protons.

Particular calcium phosphate compounds are tricalcium phosphate (TCP) ($Ca_3(PO_4)_2$), apatite ($Ca_5(PO_4)_3X$ with X being F, Cl, OH) and hydroxyapatite (HA), an apatite wherein the extra ion is mainly hydroxide.

Other calcium phosphate compounds are amorphous calcium phosphate (ACP), ($Ca_x(PO_4)_y.H_2O$), monocalcium phosphate monohydrate (MCPM) ($CaH_4(PO_4)_2.H_2O$), dicalcium phosphate dihydrate (DCPD) ($CaHPO_4.2H_2O$) also called brushite, dicalcium phosphate anhydrous (DCPA) ($CaHPO_4$) also called monetite, precipitated or calcium-deficient apatite (CDA), $(Ca,Na)_{10}(PO_4,HPO_4)_6(OH)_2$ and tetracalcium phosphate (TTCP) ($Ca_4P_2O_9$) also called hilgenstockite.

The term "biocompatible" as used herein, means that the material does not elicit a substantial detrimental response in the host.

The term "bioresorbable" refers to the ability of a material to be resorbed in vivo. In the context of the present invention, "full" resorption means that no significant extracellular fragments remain. The resorption process involves elimination of the original implant materials through the action of body fluids, enzymes or cells.

Resorbed calcium phosphate may, for example, be redeposited as new bone mineral via osteoblastic cells action, or by being otherwise, reutilized within the body or excreted. "Strongly bioresorbable" means that a major part of the calcium phosphate implant is resorbed between one and five years. This delay depends not only on intrinsic features of the calcium phosphate implant but also on the implanted site, age of the patient, primary stability of implant etc. . . . .

In the context of the present invention, a "calcium phosphate cement" (CPC) is a solid composite material comprising or made of one or more calcium phosphates eventually with additional calcium salts which sets and hardens in presence of water or an aqueous solution. The term refers to the paste resulting from the mixing of the solid material with the water or the aqueous solution as well as to the hardened material obtained after setting. Other additives may be included in small amounts to adjust the properties of the cement such as the setting time, the viscosity, reduce cohesion or swelling time, and/or induce macroporosity, and confer elasticity to the final hardened product.

In the context of the present invention, the "setting" of a cement means the hand-off self-hardening of the cement paste at ambient temperature, that is, depending on the environment, room temperature or body temperature.

In the context of the present invention, an "injectable cement" or a "cement in a form suitable to be injected" refers to a cement paste which may be pushed through a needle with a diameter of a few millimetres, preferably between 1 and 5 mm, more preferably between 1 and 3 mm, most preferably between 2 and 3 mm. Particularly important parameters for injectable cements include the absence of large particles, a suitable viscosity as well as an appropriate setting time in vivo (at 37° C.).

Gallium Doped Phosphocalcic Compound

According to a first aspect, the invention thus relates to a gallium-doped phosphocalcic compound of formula (I):

wherein $0 < x < 1$
and the salts, hydrates and mixtures thereof.

The salts may be in particular compounds of formula (I) wherein the calcium is partially replaced by other elements such as Zn, Cu, Mg, Na, K.

Preferably, the value of x in formula (I) is $0 < x \leq 0.85$, and even more preferably $0 < x \leq 0.82$.

According to particular embodiments of the invention, the gallium-doped phosphocalcic compound according to the invention is selected from the group consisting of $Ca_{10.125}Ga_{0.25}(PO_4)_7$, $Ca_{9.75}Ga_{0.5}(PO_4)_7$, $Ca_{9.375}Ga_{0.75}(PO_4)_7$, $Ca_{9.27}Ga_{0.82}(PO_4)_7$.

The gallium doping and the presence of the phosphocalcic support can be evidenced by powder X-ray diffraction and $^{31}P$ and $^{71}Ga$ solid state NMR, the two latter methods showing both. Indeed, replacement of calcium by gallium results in an upfield shift of the $^{31}P$ NMR lines related to the phosphate groups bound to gallium, while the coordination geometry of gallium can be obtained from the $^{71}Ga$ chemical shift value.

Without wishing to be bound to any theory, the inventors believe that the gallium ions are at least partially incorporated into the phosphocalcic compound by replacement of Ca(II) ions by Ga(III) ions in the crystal lattice and creation of vacancies to compensate for the difference in cation charge. Because the ionic radius of Ga(III) ions is smaller than that of Ca(II) ions, the replacement reaction is expected to lead to the contraction of the unit cell. The gallium-doped compounds are thus likely to present a deformed structure.

The preferred gallium-doped phosphocalcic compounds are based on the β-TCP or CDA structures.

The gallium-doped phosphocalcic compound may be totally or partially amorphous, but it is preferably at least partially crystalline. In particular, the phosphocalcic compound may contain one or more crystalline phases.

The crystalline phases of the gallium-doped phosphocalcic compounds may be in particular related to β-tricalcium phosphate (β-TCP) (Dickens, B. et al., 1974; Yashima, M. et al., 2003).

Tricalcium phosphate (TCP) has the formula $Ca_3(PO_4)_2$ and is also known as calcium orthophosphate, tertiary calcium phosphate tribasic calcium phosphate or bone ash. The. β-TCP form crystallises in the space group R3c and has the following cell parameters: a=10.435 Å, c=37.403 Å, α=90°; β=90° and γ=120°.

The gallium is preferably included in the crystal lattice of the phosphocalcic compound. In this case, it is particularly preferred that the gallium ions occupy the calcium sites.

However, it has been observed that gallium-doped phosphocalcic compounds obtained at low temperature may comprise gallium species adsorbed at the surface. Heating such compounds generally leads to the diffusion of the gallium into the crystal structure.

Preparation of Gallium-Doped Phosphocalcic Compounds

According to a second aspect, the invention concerns a process for the manufacture of gallium-doped phosphocalcic compounds as described above.

In fact, two different processes have been developed and are described hereafter, a solid-state process and a process in solution.

A further object of the present invention thus relates to a solid state process for the manufacture of a gallium-doped phosphocalcic compound of formula (I) comprising the steps of:

(a) contacting calcium phosphate with calcium carbonate in presence of a suitable quantity of a gallium compound;
(b) sintering the mixture to form a gallium-doped phosphocalcic compound; and
(c) recovering the gallium-doped phosphocalcic compound.

The process is preferably carried out in absence of water. Therefore, the use of anhydrous calcium phosphate such as DCPA or DCPD or a mixture thereof is preferred. For the same reason, the reactants are preferably anhydrous compounds.

The calcium carbonate is decomposed to yield carbon dioxide and thus limiting contamination of the sample with undesired anions.

Preferred gallium compounds of use in step (a) of the process are chosen among those that are non volatile and stable at ambient conditions, and include in particular gallium oxide and precursors transformed into oxides during sintering such as gallium hydroxide.

In case the gallium is incorporated in form of its oxide, the reaction can be represented by the following equation:

$$7CaHPO_4 + (3.5-1.5x)CaCO_3 + (x/2)Ga_2O_3 \rightarrow Ca_{10.5-1.5x}Ga_x(PO_4)_7 + 3.5H_2O + (3.5-1.5x)CO_2$$

with $0<x<1$

The process is preferably conducted using stoechiometric quantities of the reactants.

The temperature at step (b) is chosen preferably to be close or above the fusion temperature of the reactants. Generally, a temperature of 750° C. to 1570° C., preferably 800° C. to 1550° C., in particular 900° C. and 1360° C. and in particular 1000° C. is appropriate.

Preferably, step (b) is carried out until complete sintering, typically during a period of time of more than 12 hours, more preferably of 24 hours or more.

A further object of the present invention relates to a gallium-doped phosphocalcic compound obtainable according to the solid-state process according to the invention.

The process will yield the modified phosphocalcic compound under the crystal form which is formed under the process conditions. More specifically, the process described will yield gallium-doped phosphocalcic compound with a structure close to β-TCP. Such structure shows a R3c space group, with cell parameters varying in the following range, as a function of the Ga content: a=10.31-10.44 Å, c=37.15-37.5 Å, α=90°; β=90° and γ=120°.

A further object of the present invention relates to a process in solution for the manufacture of gallium-doped phosphocalcic compounds.

Therefore, the invention also relates to a process for providing a gallium-doped phosphocalcic compound as described by precipitation out of an aqueous solution containing gallium, calcium and phosphate ions, preferably by way of lowering the pH.

More specifically, the process for the manufacture of a gallium-doped compound according to the invention comprises the steps consisting of:

(a) preparing an aqueous solution containing a calcium compound and an appropriate quantity of a gallium compound;
(b) adjusting the pH of the solution obtained in step (a) to a value of 8.5 to 12, preferably 9 to 11, more preferably 9 to 9.5, if necessary;
(c) adding to said solution an appropriate quantity of a phosphate compound;
(d) precipitating a gallium-doped phosphocalcic compound by adjusting the pH of said solution to a value of 7.0 to 12, preferably 7.5 to 9, more preferably 7.5 to 8; and
(e) separating the precipitated gallium-doped phosphocalcic compound from the solution.

The calcium and gallium compounds used to prepare the solution in step (a) may be chosen from a wide variety of water soluble compounds such as salts or complexes.

Preferably, said gallium compound in step (a) is selected from the group consisting of gallium acetate, gallium carbonate, gallium citrate, gallium chloride, gallium bromide, gallium iodide, gallium fluoride, gallium formate, gallium nitrate, gallium oxalate, gallium sulfate, a gallium oxide or hydroxide, and their hydrates. Particularly preferred is gallium nitrate, in view of its high solubility.

Preferably, the calcium compound is selected from the group consisting of calcium nitrate, calcium acetate, calcium chloride and calcium fluoride, and their hydrates. As for the gallium compound, calcium nitrate, and especially calcium nitrate tetrahydrate, is particularly preferred because of its high solubility.

In order to enhance purity of the prepared compound, it is preferred to use ultrapure water to prepare the solutions used in the process. "Ultrapure water" means water having a resistivity of at least 18 MΩ cm.

Step (b) is conveniently carried out by adding a pH adjusting agent such as a base or an acid. Preferred are strong bases and acids which do not introduce further ions. An appropriate pH adjusting agent is an ammonia solution.

The phosphate compound used in step (c) may be any soluble salt or complex containing the phosphate anion of the gallium-doped compound envisaged.

Such a salt may be conveniently a hydrogen phosphate salt. Most preferably, the cation is volatile, for example ammonium, in order to avoid any contamination of the compound by replacement of calcium with other cations and thus ensure a high purity of the compound. Ammonium hydrogen phosphate is thus particularly preferred as a phosphate compound in the process according to the invention. Advantageously, the salt is previously dissolved in water.

During step (c), the solution turns white upon the starting of the precipitation of the gallium-doped phosphocalcic compound.

In order to ensure a homogeneous concentration of the reactants, the reaction mixture is preferably stirred during step (c) and (d).

The molar ratio of the reactants is preferably stoechiometric and thus depends mainly on the ratio (Ca+Ga)/P required.

In order to speed up the reaction, the precipitation in step (d) is preferably carried out at elevated temperature between 20 and 100° C., more preferably between 37 and 80° C., the most preferably at 50° C.

The pH adjusting agent used in step (d) is again preferably a compound which does not add any further ions to the reaction mixture. Particularly preferred is an ammonia solution.

The reaction proceeds smoothly within minutes or hours. Preferably, the step (d) is carried out for a period of time between 15 min and 72 h, more preferably between 30 min and 6 hours, still more preferably between 30 min and 2 hours, most preferably 30 min.

After completion of the reaction, the precipitate is separated in step (e) from the reaction mixture by conventional means, such as filtration.

Subsequently, the obtained gallium-doped phosphocalcic compound may be further purified and/or transformed. In particular, the compound obtained at step (e) may be purified, in particular be washed and dried. The raw product may in particular be washed with ultrapure water and subsequently dried at a suitable temperature, such as 80° C.

The phosphocalcic compound thus obtained has generally a structure similar to calcium deficient apatite (CDA) structure, evidenced by a Ca/P ratio in the 1.44-1.67 range, a $^{31}$P NMR broad resonance at 2.9 ppm, characteristic X-ray powder diffraction broad lines (2θ=~26° (medium) and ~32° (strong)) and IR absorptions [OH (~3570 cm$^{-1}$) and PO$_4$ (~1040 and 1100 cm$^{-1}$)]. The gallium may be included within the crystal or be present on its surface either as physically sorbed, chemically sorbed or precipitated gallium species.

A further object of the present invention relates to a gallium-doped phosphocalcic compound obtainable by the method described above.

A further object of the present invention relates to a gallium-doped phosphocalcic compound obtainable by the process described, with a (Ca+Ga)/P molar ratio in the range of 1.3 to 1.67, and a gallium content up to 4.5% by weight.

The gallium-doped phosphocalcic compound obtained may be subsequently calcinated to obtain a gallium-doped compound with a β-TCP-like structure, for example by heating it to a temperature of typically between 800 and 1500° C., more preferably between 900 and 1300° C., most preferably at 1100° C., preferably for a period of time of several hours, especially 3 hours to 5 hours, typically 4 hours. Indeed, using this process, a stoechiometric quantity of gallium compound lead for example to compounds of formula (I) with x≤0.75.

The gallium-doped phosphocalcic compounds thus obtained are particularly useful for dental and medical applications relating in particular to bone repair, augmentation, reconstruction, regeneration, and osteoporosis treatment.

More specifically, the compounds according to the invention may be used for the manufacture of biomaterials such as bone substitutes, implant coatings, compacted or moulded phosphocalcic implants, composite phosphocalcic-polymer cements and calcium-phosphate cements.

The invention will be further illustrated in view of the following figures and examples.

FIGURES

Figure 2:
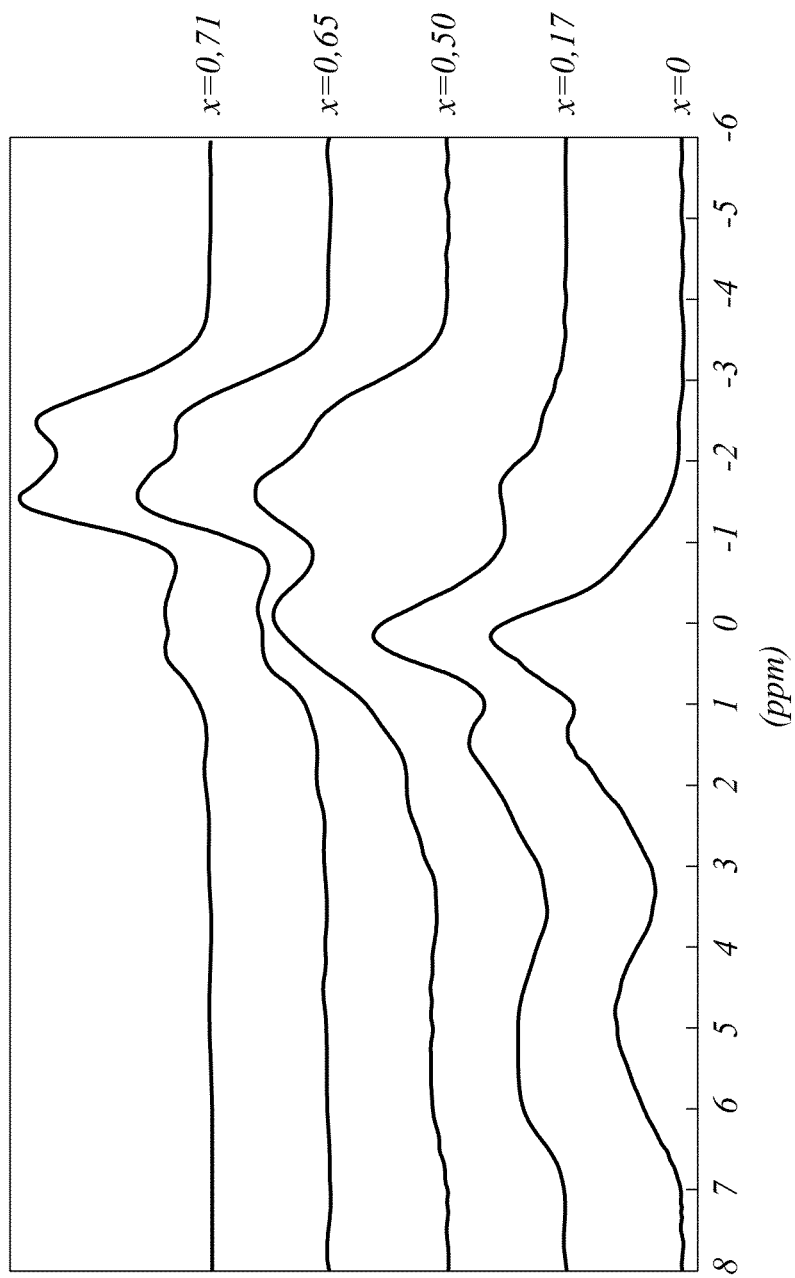
Figure 3:
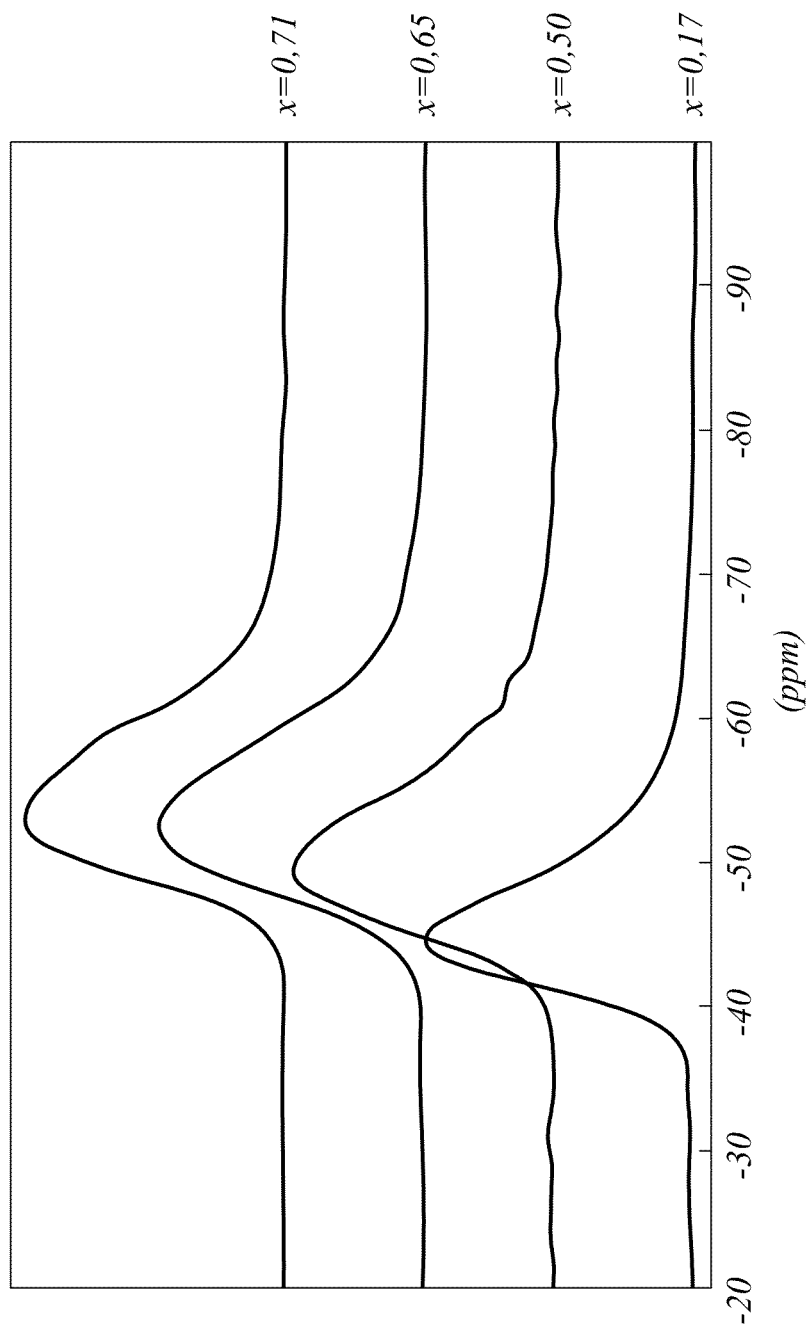

FIG. 1: X-Ray microradiography of a gallium-doped phosphocalcic compound prepared according to example 1 (top) versus TCP without Ga (bottom) showing the higher radio-opacity of compound according to the invention;

FIG. 2: $^{31}$P MAS NMR spectra of powdered samples of Ca$_{10.5-1.5x}$Ga$_x$(PO$_4$)$_7$ for different values of x, recorded at 7.0 T using a 4 mm probehead and ZrO$_2$ rotors;

FIG. 3: $^{71}$Ga echo MAS NMR spectra of powdered samples of Ca$_{10.5-1.5x}$Ga$_x$(PO$_4$)$_7$ for 0.17<x<0.71, recorded at 17.6 T; and FIG. 4: $^{31}$P MAS NMR spectrum of a powdered sample of the gallium-doped CDA isolated for an initial Ga/P ratio of 0.07, recorded at 7.0 T. After calcination at 1000° C., Ca$_{9.75}$Ga$_{0.05}$(PO$_4$)$_7$ was obtained.

EXAMPLES

Example 1

Preparation of Gallium-Doped Calcium Phosphate by Solid State Reaction

In a mortar, anhydrous calcium phosphate (0.174 mol) was intimately mixed with the quantity of calcium carbonate and gallium oxide calculated such that the (Ca+Ga)/P molar ratio corresponds to the desired x value using the equation below.

Calcination of the mixture in a crucible, typically on a 5 gram preparation scale, was performed at 1000° C. for 24 hours (heating rate: 5° C./min, cooling rate 5° C./min).

$$7CaHPO_4+(3.5-1.5x)CaCO_3+x_{/2}Ga_2O_3 \rightarrow Ca_{10.5-1.5x}Ga_x(PO_4)_7+3.5H_2O+(3.5-1.5x)CO_2$$

The structure of the compound was obtained by Rietveld refinement from X-ray powder diffraction patterns, recorded using a Philips PW 1830 generator equipped with a vertical PW 1050 (θ/2θ) goniometer and a PW 1711 Xe detector. The data were acquired using a Ni filtered copper Kα radiation in a step by step mode with: 2θ initial: 10°, 2 θ final: 100°, step 2θ=0.03°, time per step: 2.3 seconds.

The atomic coordinates for Ca$_{9.27}$Ga$_{0.82}$(PO$_4$)$_7$ thus obtained are indicated in table 1. From the data obtained, it is apparent that the compound has a β-TCP-type structure wherein one of the 5 calcium sites is gradually replaced by gallium, while a second calcium site empties for charge compensation. The space group is R3c with a=10,322 Å, c=37, 179 Å, α=90°; β=90° and γ=120°.

The $^{31}$P MAS NMR spectra recorded at 7.0 T using a 4 mm probehead and ZrO$_2$ rotors (FIG. 2) were taken from the compounds. The spectra show an upfield shift of the NMR peaks as the number of phosphate sites bound to gallium increases.

The $^{71}$Ga echo MAS NMR spectra of Ca$_{10.5-1.5x}$Ga$_x$(PO$_4$)$_7$ (FIG. 3) recorded at 17.6 T. The spectra show the presence of gallium ions in the compounds, with an isotropic chemical shift characteristic of a GaO$_6$ environment [−38 to −46 ppm], in agreement with the X-ray structure determination.

TABLE 1

Refined atomic coordinates for Ca$_{9.27}$Ga$_{0.82}$(PO$_4$)$_7$

| Atom | Wyckoff Position | Site | Occupancy | x/a | y/b | z/c | U [Å$^2$] |
|---|---|---|---|---|---|---|---|
| Ca1 | 18b | 1 | | 0.7226 (5) | 0.8565 (7) | 0.1656 (2) | 0.0096 (6) |
| Ca2 | 18b | 1 | | 0.6215 (5) | 0.8243 (8) | −0.0348 (2) | 0.0096 (6) |
| Ca3 | 18b | 1 | | 0.1303 (6) | 0.2781 (4) | 0.0589 (2) | 0.0096 (6) |
| Ga | 6a | 3 | 0.817 | 0 | 0 | −0.26632 | 0.0055 (14) |
| Ca5 | 6a | 3 | 0.183 | 0 | 0 | −0.26632 | 0.0055 (14) |
| Ca4 | 6a | 3 | 0.092 | 0 | 1.00000 | −0.061 (2) | 0.0096 (6) |

TABLE 1-continued

Refined atomic coordinates for $Ca_{9.27}Ga_{0.82}(PO_4)_7$

| Atom | Wyckoff Position | Site | Occupancy | x/a | y/b | z/c | U [Å²] |
|---|---|---|---|---|---|---|---|
| P1  | 6a  | 3 |   | 0          | 0          |  0.0000 (3) | 0.0068 (9)  |
| P2  | 18b | 1 |   | 0.6828 (6) | 0.8580 (8) | −0.1303 (2) | 0.0068 (9)  |
| P3  | 18b | 1 |   | 0.6553 (8) | 0.8476 (9) | −0.2359 (2) | 0.0068 (9)  |
| O1  | 6a  | 3 |   | 0          | 0          |  0.0449 (5) | 0.0045 (10) |
| O2  | 18b | 1 |   | 0.0169 (14)| 0.8634 (11)| −0.0099 (4) | 0.0045 (10) |
| O3  | 18b | 1 |   | 0.7364 (13)| 0.9132 (13)| −0.0922 (4) | 0.0045 (10) |
| O4  | 18b | 1 |   | 0.751 (2)  | 0.7672 (18)| −0.1455 (4) | 0.0045 (10) |
| O5  | 18b | 1 |   | 0.726 (2)  | 0.0002 (16)| −0.1529 (4) | 0.0045 (10) |
| O6  | 18b | 1 |   | 0.5058 (14)| 0.758 (2)  | −0.1324 (4) | 0.0045 (10) |
| O7  | 18b | 1 |   | 0.6084 (16)| 0.9581 (16)| −0.2217 (4) | 0.0045 (10) |
| O8  | 18b | 1 |   | 0.5840 (17)| 0.6940 (18)| −0.2130 (4) | 0.0045 (10) |
| O9  | 18b | 1 |   | 0.8297 (15)| 0.921 (2)  | −0.2288 (4) | 0.0045 (10) |
| O10 | 18b | 1 |   | 0.6264 (12)| 0.8208 (16)|  0.7249 (4) | 0.0045 (10) |

Example 2

Preparation of Gallium Doped Calcium Phosphate by Coprecipitation

For a product with a (Ca+Ga)/P molar ratio of 1.5, a mixture of 0.444 g gallium nitrate (Aldrich, MW=390) and 2.685 g calcium nitrate tetrahydrate (MW=236) are dissolved in a beaker containing 125 mL of ultrapure water.

The pH of the solution is adjusted in the 9-9.5 range by means of a concentrated solution of ammonia. The reaction mixture is then introduced in a three-neck angled round bottom flask placed in an oil bath and equipped with a dropping funnel. Into the dropping funnel are introduced 1.089 g of diammonium hydrogen phosphate (MW=132) dissolved in 125 mL of ultrapure water. The temperature of the reaction mixture is raised to 50° C. and the solution of diammonium hydrogen phosphate is added dropwise over a 5-10 minutes period. The mixture turns white. The pH is adjusted in the 7.5-8 range by means of a concentrated solution of ammonia (initial time of reaction). After 30 minutes, the heater is stopped and the suspension (pH is neutral) is centrifuged. The main part of the supernatant is removed and the solid residue is washed with 250 mL of ultrapure water, centrifuged and again separated from the main part of the supernatant. After repeating this procedure four times, the final solid is filtered off. The white waxy product is dried in the oven at 80° C. during 24 hours.

Figure 4:
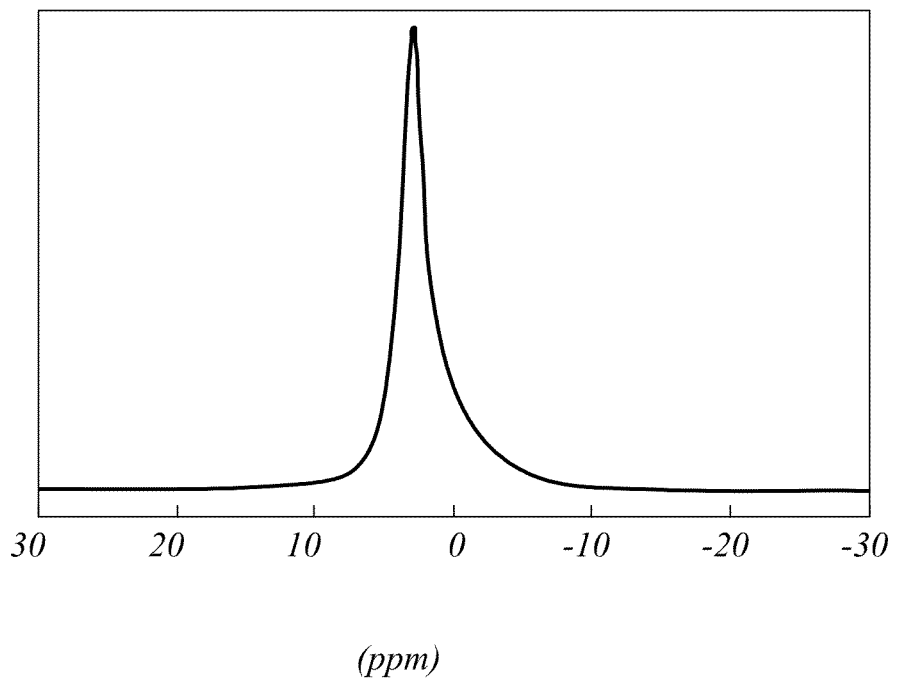

The compounds were characterized by IR spectroscopy [OH (~3570 cm$^{-1}$) and PO$_4$ (~1040 and 1100 cm$^{-1}$)], powder X-ray diffraction [broad lines at 2θ=~26° (medium) and ~32° (strong)] and $^{31}$P MAS NMR spectroscopy [broad resonance at 2.9 ppm] before calcination at 1000° C. (FIG. 4). The corresponding data are characteristic of a calcium deficient apatite.

This was also confirmed by elemental analysis which showed a (Ca+Ga)/P molar ratio in the 1.3-1.5 range and a gallium content up to 4.5% by weight. After calcination at 1000° C., the resulting compounds correspond to those obtained in example 1 (x=0-0.75), as confirmed by powder X-ray diffraction and solid state $^{31}$P and $^{71}$Ga NMR, indicating a structure close to β-TCP. For large amounts of gallium nitrate (initial Ga/P ratio>about 0.15), the presence of by-products (mainly gallium oxide) mixed with the gallium-doped TCP phase was observed in the calcined compound.

REFERENCES

Bernstein L. R., *Pharmacological Reviews* 1998, 50, (4), 665-682.
Blumenthal N C and Cosma V (1989) Bull Hosp Jt Dis Orthop Inst 49: 192-204
Bockman R S and Bosco B (1994), Semin Arthritis Rheum 23: 268-269
Bockman R S et al. (1989), *J Bone Miner Res* 4: S167.
Bockman R S et al. (1995) J Clin Endocrinol Metab 80:595-602.
Dickens B. et al. (1974) J Solid State Chem 10, 232
Donnelly R., et al. Calcif Tissue Int., 1993. 53(6): p. 400-10
Donnelly R. and Boskey A. (1989), Calcif Tissue Int 44: 138-142
Dudley H C and Maddox G E (1949) *J Pharmacol Exp Ther* 96: 224-227
Golubev et al. Neorganicheskoi khimii 35, (12): 3037-3041, December 1990.
Korbas et al. J Biol Inorg Chem (2004) 9:67-76.
Nelson B et al. J Nucl Med (1972) 13: 92-100
Valappil S P et al Acta Biomaterialia (2008), doi: 10.1016/j.actbio.2008.09.019
Warrell R P Jr (1995) in Handbook of Metal-Ligand Interactions in Biological Fluids, Bioinorganic Medicine (Berthon G ed) vol 2, pp 1253-1265, Marcel Dekker, New York.
Warrell R P Jr et al. (1987) J Clin Oncol 5: 292-298.
Warrell R P Jr and Bockman R S (1989) in Important Advances in Oncology 1989 (DeVita V T, Hellman S and Rosenberg S A eds) pp 205-220, J.B. Lippincott, Philadelphia.
Warrell R P et al. (1984) J Clin Invest 73: 1487-1490.
Warrell R P Jr, et al. (1985) Cancer Treat Rep 69: 653-655.
Warrell R P Jr et al., (1993) J Clin Oncol 11: 2443-2450.
Yashima M. et al. (2003) J Solid State Chem 175, 272.

We claim:

1. A process in solution for the manufacture of a gallium-doped phosphocalcic compound of formula (I): $Ca_{(10.5-1.5x)}Ga_x(PO_4)_7$ having a structure close to β-tricalcium phosphate (β-TCP), wherein 0<x<1 and the salts, hydrates and mixtures thereof, comprising the following steps:
   (a) preparing an aqueous solution containing a calcium compounds and an appropriate quantity of a gallium compound;
   (b) adjusting the pH of the solution obtained in step (a) to a value of 8.5 to 12;
   (c) adding to said solution an appropriate quantity of a phosphate compound;

(d) precipitating the gallium doped phosphocalcic compound by adjusting the pH of the obtained solution to a value of 7.0 to 12;
(e) separating the precipitated gallium doped phosphocalcic compound from the solution; and
(f) calcining the gallium doped phosphocalcic compound obtained.

2. The process in solution according to claim 1, wherein said gallium salt in step (a) is selected from the group consisting of gallium acetate, gallium carbonate, gallium citrate, gallium chloride, gallium fluoride, gallium formate, gallium nitrate, gallium oxalate, gallium sulfate, gallium hydroxide, and gallium oxide hydroxide.

3. The process in solution according to claim 1, wherein said calcium solid precursor in step (a) is selected from the group consisting of calcium nitrate tetrahydrate, calcium acetate, calcium chloride and calcium fluoride.

4. The process in solution according to claim 1, wherein the phosphate compound is ammonium hydrogen phosphate.

5. The process in solution according to claim 1, wherein step (d) is carried out at a temperature between 37 and 80° C.

* * * * *